(12) United States Patent
Harr

(10) Patent No.: US 8,241,018 B2
(45) Date of Patent: Aug. 14, 2012

(54) COMPACT PERISTALTIC MEDICAL PUMP

(75) Inventor: James Harr, Foristell, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 281 days.

(21) Appl. No.: 12/557,351

(22) Filed: Sep. 10, 2009

(65) Prior Publication Data

US 2011/0060284 A1    Mar. 10, 2011

(51) Int. Cl.
*F04B 45/06*    (2006.01)

(52) U.S. Cl. .............. 417/477.14; 604/67; 604/132

(58) Field of Classification Search .......... 600/431–435; 604/65–67, 131–134, 151–155; 417/477.14
See application file for complete search history.

(56) References Cited

U.S. PATENT DOCUMENTS

| | | |
|---|---|---|
| 249,285 A | 11/1881 | Allen |
| 2,466,618 A | 4/1949 | Stocks |
| 2,483,924 A | 10/1949 | Moulinier |
| 2,990,048 A | 6/1961 | Paton |
| 3,101,674 A | 8/1963 | Weiskopf et al. |
| 3,306,229 A | 2/1967 | Smythe |
| 3,523,000 A | 8/1970 | Miller |
| 3,582,234 A | 6/1971 | Isreeli et al. |
| 3,588,281 A | 6/1971 | Isreeli et al. |
| 3,628,891 A | 12/1971 | Isreeli et al. |
| 3,712,762 A | 1/1973 | Kenney |
| 3,758,239 A | 9/1973 | Hrdina |
| 3,791,400 A | 2/1974 | Hrdina |
| 3,862,780 A | 1/1975 | Senn |
| 4,006,736 A | 2/1977 | Kranys et al. |
| 4,256,437 A | 3/1981 | Brown |
| 4,529,106 A | 7/1985 | Broadfoot et al. |
| 4,544,336 A | 10/1985 | Faeser et al. |
| 4,715,435 A | 12/1987 | Foret |
| 4,722,734 A | 2/1988 | Kolln |
| 4,735,553 A | 4/1988 | Vidal |
| 4,813,420 A | 3/1989 | Nunogaki |
| 4,878,622 A | 11/1989 | Jamison et al. |
| 4,884,013 A | 11/1989 | Jackson et al. |
| 4,913,625 A | 4/1990 | Gerlowski |
| 4,950,235 A | 8/1990 | Slate et al. |

(Continued)

FOREIGN PATENT DOCUMENTS

EP    2077129 A1    7/2009

(Continued)

OTHER PUBLICATIONS

European Search Report regarding related application serial No. EP 10008823.6 dated Dec. 2, 2010, 6 pgs.

*Primary Examiner* — Jacki Ho
*Assistant Examiner* — Gerald Landry, II
(74) *Attorney, Agent, or Firm* — Elias Domingo, Esq.

(57) ABSTRACT

A compact medical pump includes a linear peristaltic pumping mechanism driven by a motor located within a periphery of a belt of the pumping mechanism. The motor drives a gear set that drives a driving pulley which engages the belt having the rollers. A battery for the pump is positioned adjacent to the gear set. The pump includes a controller and user interface for operating the pumping mechanism as a function of pumping parameters input via the user interface. The controller may sense motor current and determine fluid path characteristics based on the sensed current.

10 Claims, 7 Drawing Sheets

U.S. PATENT DOCUMENTS

| | | | |
|---|---|---|---|
| 4,982,903 A | 1/1991 | Jamison et al. | |
| 5,015,151 A | 5/1991 | Snyder, Jr. et al. | |
| 5,059,171 A | 10/1991 | Bridge et al. | |
| 5,074,756 A | 12/1991 | Davis | |
| 5,103,211 A * | 4/1992 | Daoud et al. | 340/608 |
| 5,131,816 A | 7/1992 | Brown et al. | |
| 5,176,646 A | 1/1993 | Kuroda | |
| 5,370,510 A | 12/1994 | Sinclair et al. | |
| 5,499,969 A * | 3/1996 | Beuchat et al. | 604/30 |
| 5,601,413 A | 2/1997 | Langley et al. | |
| 5,649,808 A * | 7/1997 | Gruszecki et al. | 417/63 |
| 5,791,881 A * | 8/1998 | Moubayed et al. | 417/63 |
| 5,803,712 A | 9/1998 | Davis et al. | |
| 5,813,842 A | 9/1998 | Tamari | |
| 5,901,698 A | 5/1999 | Welles | |
| 5,935,099 A | 8/1999 | Peterson et al. | |
| 5,965,089 A | 10/1999 | Jarvik et al. | |
| 6,023,401 A | 2/2000 | Hashimoto et al. | |
| 6,164,921 A * | 12/2000 | Moubayed et al. | 417/44.1 |
| 6,402,478 B1 | 6/2002 | Zhang et al. | |
| 6,485,465 B2 | 11/2002 | Moberg et al. | |
| 6,527,745 B1 | 3/2003 | Kanda et al. | |
| 6,554,025 B1 | 4/2003 | Fitter | |
| 6,555,986 B2 | 4/2003 | Moberg | |
| 6,585,675 B1 | 7/2003 | O'Mahony et al. | |
| 6,656,148 B2 | 12/2003 | Das et al. | |
| 6,659,980 B2 | 12/2003 | Moberg et al. | |
| 6,854,620 B2 | 2/2005 | Ramey | |
| 6,896,429 B2 | 5/2005 | White et al. | |
| 6,923,782 B2 | 8/2005 | O'Mahony et al. | |
| 6,966,895 B2 | 11/2005 | Tribe | |
| 6,993,795 B2 | 2/2006 | Prineppi | |
| 2002/0094277 A1 | 7/2002 | Gaudet et al. | |
| 2002/0151804 A1 | 10/2002 | O'Mahony et al. | |
| 2004/0030277 A1 | 2/2004 | O'Mahony et al. | |
| 2004/0106902 A1 | 6/2004 | Diaz et al. | |
| 2004/0127840 A1 * | 7/2004 | Gara et al. | 604/4.01 |
| 2004/0133166 A1 | 7/2004 | Moberg et al. | |
| 2004/0191116 A1 | 9/2004 | Jarvik et al. | |
| 2005/0047946 A1 * | 3/2005 | Davis et al. | 417/477.11 |
| 2005/0127865 A1 | 6/2005 | Kiuchi et al. | |
| 2005/0209563 A1 * | 9/2005 | Hopping et al. | 604/151 |
| 2006/0136081 A1 * | 6/2006 | DiGianfilippo et al. | 700/95 |
| 2006/0219644 A1 * | 10/2006 | O'Hara et al. | 210/782 |
| 2007/0106218 A1 * | 5/2007 | Yodfat et al. | 604/131 |
| 2008/0051716 A1 * | 2/2008 | Stutz | 604/151 |
| 2009/0087326 A1 * | 4/2009 | Voltenburg et al. | 417/477.2 |

FOREIGN PATENT DOCUMENTS

WO    2008024812 A2    2/2008

* cited by examiner

COMPACT PERISTALTIC MEDICAL PUMP

BACKGROUND

Compact medical pumps are highly portable, which reduces the need to limit their use to a clinical setting for many medical treatments. Compact medical pumps are generally cheaper than larger, clinical counterparts such that it is cost effective to use them in more treatments. For example, administering a drug using a pump instead of a number of injections spaced apart in time results in a more consistent treatment, which is often more effective and therefore cost effective as well. Concealing a medical pumping apparatus in the clothing of a patient allows the patient to discretely receive a continuous medical treatment at any time and in any place. Some medical fluids, such as insulin, require administering only a small amount of fluid to effectively treat the patient. A syringe pump for such fluids encloses a reservoir of fluid (e.g., a vial or cassette) and is small enough to conceal in the clothing of the patient. But other medical fluids (e.g., a feeding solution) must be supplied to a patient in larger quantities to effectively treat the patient. For example, a syringe pump that encloses a reservoir having such a relatively large volume of fluid is not easily concealable in the patient's clothing.

SUMMARY

Aspects of the invention provide a compact and highly portable medical pump that may be easily concealed within a patient's clothing. A separate reservoir containing a feeding solution, for example, may be held in one pocket of the patient's clothing while a compact pump may be located in another. Two separate components (i.e., the pump and the reservoir) can be concealed in the clothing of the patient whereas a single unit having sufficient fluid volume and a pumping mechanism would not be concealable in the clothing of the patient. A compact pumping apparatus for use with a remote reservoir is desirable.

In one aspect, a compact medical pumping apparatus is sized such that it can be concealed in the clothes of a patient, and is capable of pumping fluid from a remote reservoir to the patient. The pump comprises a belt having fingers for compressing a tube that connects the reservoir to the patient. The fingers squeeze the tube against a platen of the pump and, as the belt travels proximate the tube, the fingers displace the fluid from the reservoir and move the fluid through the tube to the patient. Motive force is provided to the belt by a motor located within a space defined by an inner surface of the belt. A battery of the pumping apparatus is positioned adjacent a gear set that transfers the motive force from the motor to a driving pulley supporting the belt.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
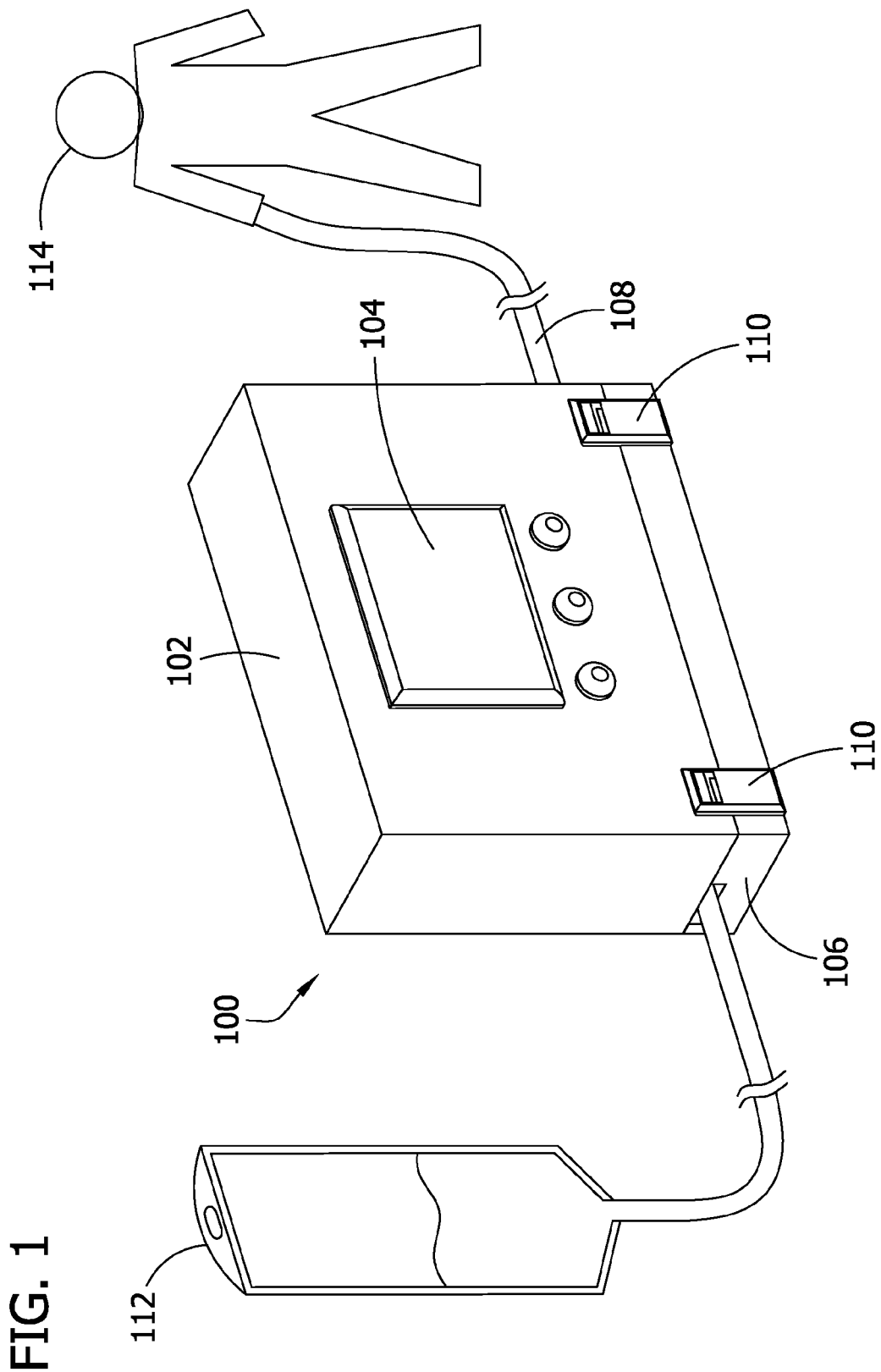
FIG. 1 is a perspective view of a compact medical pump system having a tube in communication with a fluid reservoir and positioned in a medical pump according to an embodiment of the invention.

Referring to FIG. 1, a perspective view of the front of a compact medical pumping apparatus, generally indicated at 100, is shown. The pump includes a housing 102, a user interface 104, and a platen 106. A pump set including a tube 108 for transferring fluid from a fluid source (i.e., reservoir 112) to a patient 114 is supported by a bottom portion of the housing 102 including platen 106. As is well known in the art, the tube 108 may be made of any suitable material including, for example, silicone. The platen 106 is shown attached to the housing 102 by a set of clips 110, but the platen 106 may be attached to the housing 102 by any system such as a hinge and fasteners. Advantageously, the overall size and shape of the housing 102 is compact, easily portable, and easily concealable in a user's clothing.

In operation, a user (e.g., the patient 114 or another operator) inputs a set of pumping parameters to the pump via the user interface 104. The pumping parameters indicate, for example, a rate and volume of fluid to be delivered to the patient 114, and may be for continuous fluid delivery, bolus fluid delivery, or any other fluid delivery profile known to those skilled in the art. The pump then manipulates the tube 108 to pump the medical fluid from the reservoir 112 to the patient 114 as a function of the pumping parameters. In one embodiment, the user may alter the pumping parameters at any time via the user interface 104. The user interface 104 may include provisions for preventing the user from inadvertently altering the pumping parameters (e.g., a software lockout system or a physical cover).

Figure 2:
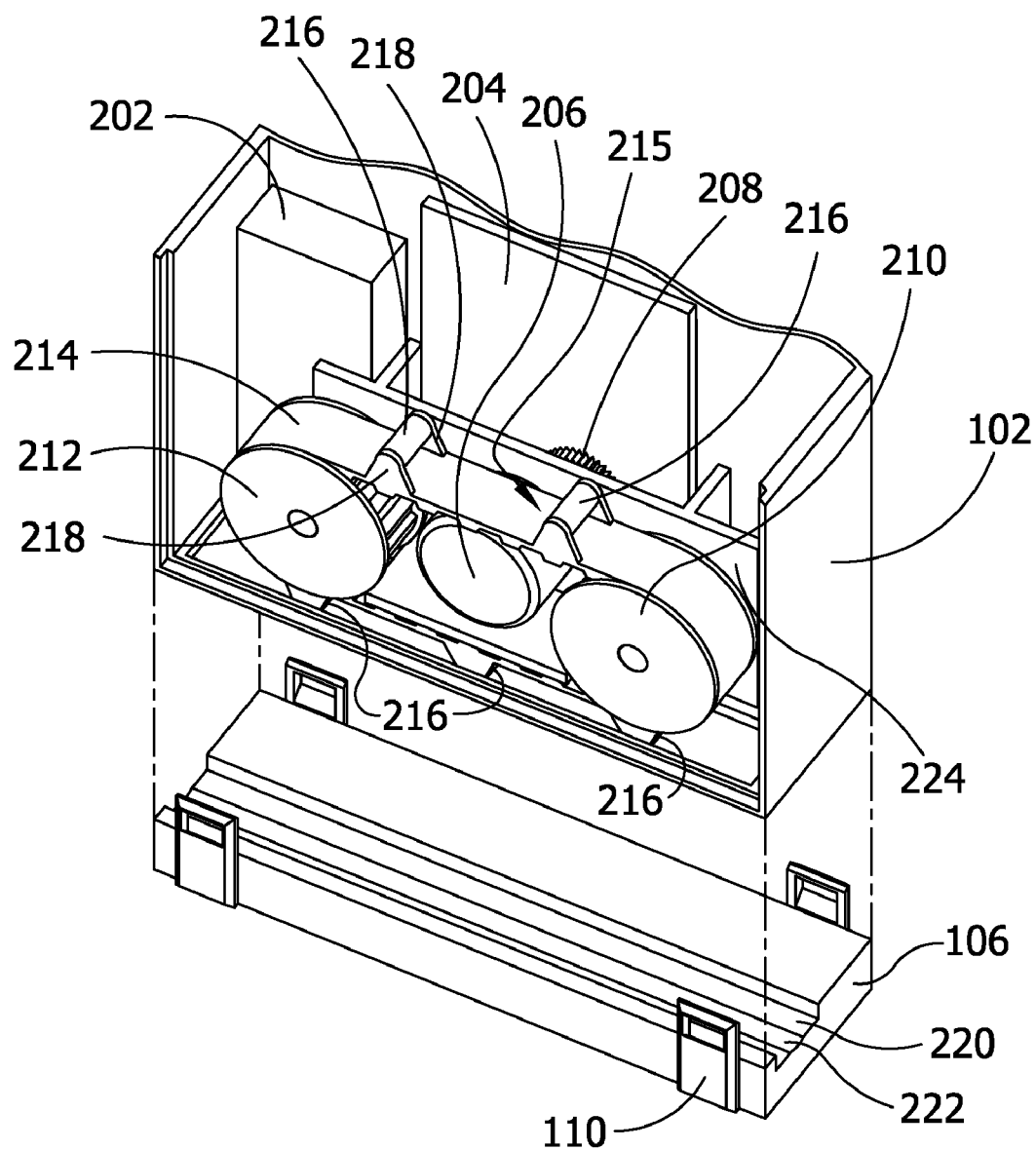
FIG. 2 is a perspective and exploded view of the compact medical pump of FIG. 1 having top and back portions of a housing of the medical pump removed.

Referring to FIG. 2, a perspective and exploded view of the back side of the compact medical pump 100 of FIG. 1 having the top and back of the housing 102 cut away is shown. A battery 202 provides power to a controller 204, and the controller 204 selectively provides power to a motor 206 in accordance with pumping parameters as determined from user input provided via the user interface 104 (see FIG. 1, not shown in FIG. 2). A gear set 208 operatively connected to the motor 206 transfers the motor's motive force to a drive pulley 210. In one embodiment, the drive pulley 210 and an idler pulley 212 support a belt 214 positioned within housing 102. The gear set 208 comprises, for example, five gears operatively connected to motor 206 and drive pulley 210 for supplying motive force from motor 206 to the belt 214. In this exemplary embodiment, a driving gear is attached to the rotor of the motor 206. An idler gear transfers motive force from the driving gear to an intermediate gear. The intermediate gear has a gear on each side of a frame member 224 supporting the gear set 208. The intermediate gear transfers motive force from the idler gear to a pulley gear, which is attached to the drive pulley 210. Other gear configurations are contemplated within the scope of the present invention.

The frame member 224, which is integral with housing 102 in the illustrated embodiment, supports the motor 206, a plurality of pulleys (e.g., pulleys 210 and 212), and gear set 208. In another embodiment, the frame member 224 is attached to housing 102 by other means such as glue, fasteners, or sonic welding. The drive pulley 210 and an idler pulley 212 engage an inner surface of belt 214. The belt 214 has grooves, and the pulleys 210, 212 have corresponding protrusions in one embodiment to prevent slippage between the belt 214 and the drive pulley 210. In other embodiments, the idler pulley 212 may be smooth (i.e., without protrusions), or both the idler 212 and driving pulley 210 may be smooth as well as the interior face of the belt 214 to form a friction fit.

The belt 214 in one embodiment has a plurality of fingers, indicated generally at 215, extending outwardly. The fingers 215 are evenly spaced about an outer surface of the belt 214 for engaging tube 108 as the belt travels. In one embodiment, each finger 215 comprises a roller 216 spaced away from the belt 214 by a standoff 218 at either end of the roller. A pin (not shown) connects the two standoffs 218 through the roller 216 to retain the roller 216 and allow the roller 216 to rotate about the pin. In another embodiment, the fingers 215 do not rotate and comprise a friction reducing material for sliding along the tube 108. The platen 106 has a groove 220 corresponding to a path in which the rollers 216 travel as belt 214 moves, and a guide channel 222 inside the groove 220 for receiving and positioning the tube 108 when the tube 108 is loaded in the pump. As belt 214 moves about pulleys 210, 212, the fingers 215 engage the tube 108, squeezing the tube 108 between the fingers 215 and an opposing surface of the guide channel 222, to generate a peristaltic pumping action within the tube 108.

Figure 3:
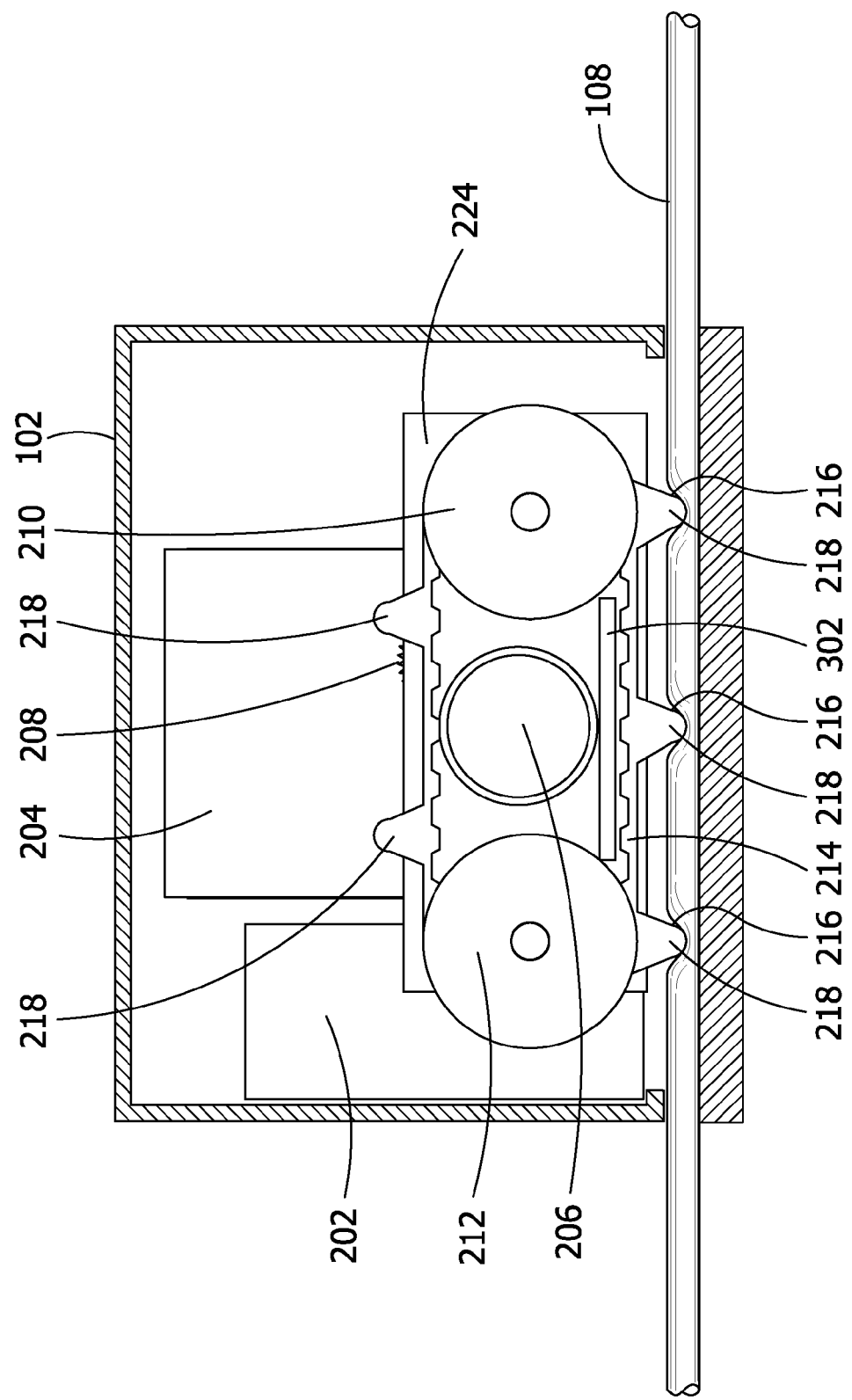
FIG. 3 is a cross section of the compact medical pump of FIG. 1 with a tube positioned in the pump.

Referring to FIG. 3, a cross section of the compact medical pump 100 of FIGS. 1 and 2 is shown from the back of the pump. In operation, the rollers 216 squeeze the tube 108 against the platen 106, occluding the tube 108 at the point where each roller 216 contacts the tube 108. As the belt 214 moves proximate the tube, the rollers 216 are moved along the tube 108, and any fluid in the tube 108 in front of the rollers 216 is forced through the tube 108 toward the patient 114. A backing plate 302 extends between the idler pulley 212 and the drive pulley 210 along the interior surface of the belt 214 such that the rollers 216 maintain sufficient pressure on the tube 108 to continuously occlude the tube 108 as they move along a length of the tube 108. The tube 108 generally returns to its original shape behind each of the rollers 216, and the resulting vacuum, or negative pressure, in tube 108 draws more fluid from the reservoir 112. The medical pump 100 encloses a limited portion of the tube 108. As each roller 216 comes to the end of the portion of the tube 108, the belt 214 lifts the roller 216 from the tube 108 and carries it back to the beginning of the portion of the tube 108 enclosed by the pump. In the illustrated embodiment, at least one roller 216 occludes the tube 108 when the tube 108 is positioned in the pump 100 for a pumping operation. The occluding roller 108 thus prevents a free flow condition from occurring (i.e., fluid flowing from the patient 114 toward the reservoir 112 or from the reservoir 112 toward the patient 114 due to a pressure difference between the reservoir 112 and the patient 114).

In one embodiment, the medical pump determines a fluid path characteristic as a function of a current of the motor 206. Fluid path characteristics include a bubble in the tube, an empty fluid source (i.e., empty reservoir), a partial occlusion in the tube, and a complete occlusion in the tube. The pump may indicate a determined fluid path characteristic to the user via the user interface 104 or alter pump operation in response to the determined fluid path characteristic in order to change the determined fluid path characteristic. For example, if the tube 108 becomes clogged or otherwise occluded (other than by the rollers 216), resistance to the movement of the rollers 216 along the tube 108 increases. The motor 206 is thus required to produce additional motive force or torque to drive the rollers 216 forward. The controller 204 includes a sensor for sensing the current through the motor 206, and because current is proportional to torque, the current through the motor 206 sensed by the controller 204 is indicative of the torque being supplied by the motor 206. If the sensed current exceeds a maximum threshold, then the controller 204 determines that there is an undesired occlusion in the tube 108 and may alert the user or patient via the user interface 104, provide an alarm, or take some other action (e.g., cease pumping), or combination of actions. The controller 204 may also take one or more corrective actions, such as reversing the flow of the fluid and then attempting to resume normal pumping operation. Reversing the flow of fluid in this manner forms a vacuum in the tube 108 downstream from the pump, possibly dislodging an occlusion in the tube 108 between the pump 100 and the patient 114. In a similar manner, controller 204 may be configured to determine the extent of an occlusion by comparing the sensed current to multiple thresholds.

If an air bubble occurs in the tube 108, resistance to the movement of the rollers 216 decreases, and the motor 206 is required to produce less torque to drive the rollers 216 forward. Thus, the current in the motor 206 and the current sensed by the controller 204 decreases. If the sensed current drops below a minimum threshold, then the controller 204 determines that there is an air bubble in the tube 108. The controller 204 may alert the user or patient via the user interface 104, provide an alarm, or take some other action (e.g., cease pumping) or combination of actions.

The controller 204 may also determine whether the reservoir 112 is empty. If the current of the motor 206 stays below a minimum threshold in excess of a predetermined period of time, indicating a relatively large amount of air in the tube 108, then the controller 204 determines that the reservoir 112 is empty. The predetermined period of time varies as a function of the pumping parameters of the pump. For example, the predetermined period of time may be shorter for a relatively high fluid delivery rate and longer for a lower fluid delivery rate. If the controller 204 determines that the reservoir 112 is empty, then it may alert the user or patient via the user interface 104, provide an alarm, or take some other action (e.g., cease pumping) or combination of actions.

Figure 4:
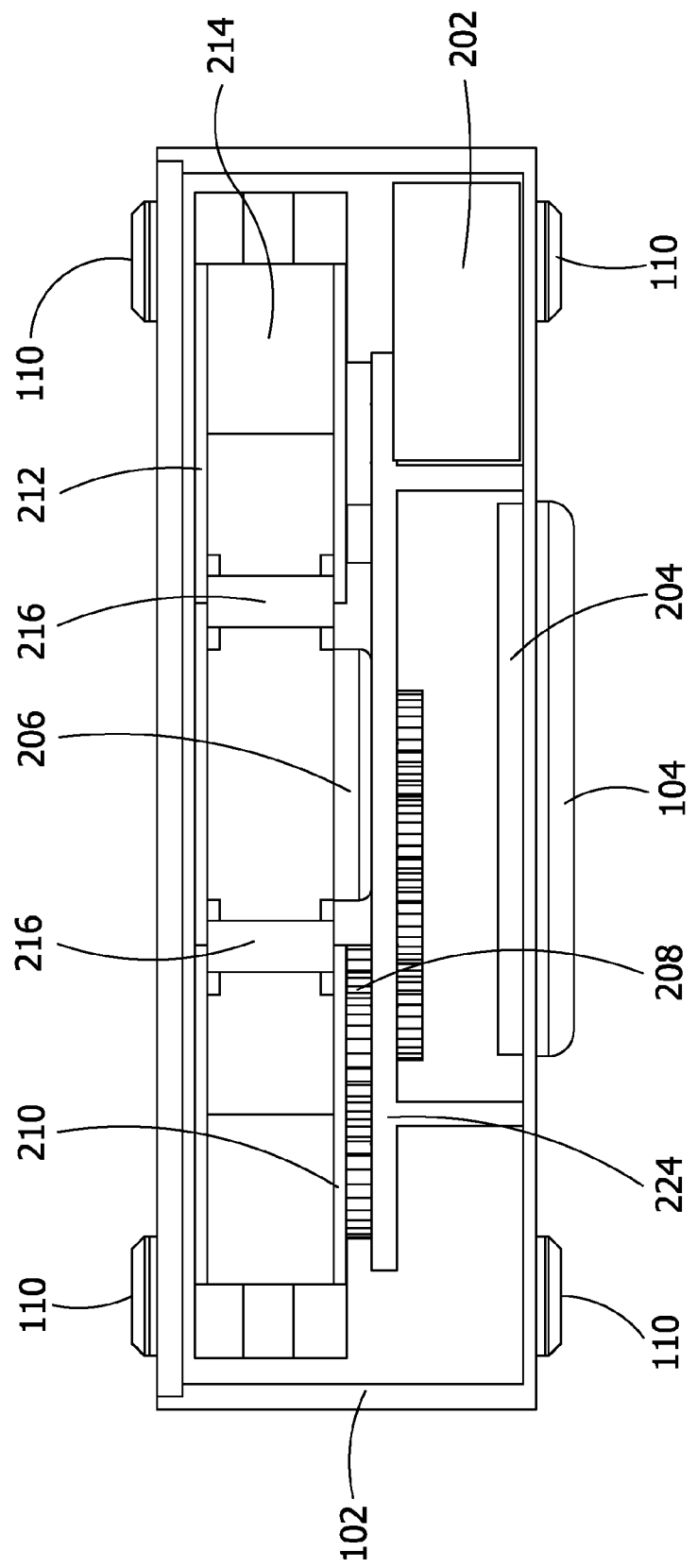
FIG. 4 is a top view of the compact medical pump of FIG. 1 having a top portion of a housing of the medical pump removed.

Referring to FIG. 4, a top view of the compact medical pump of FIGS. 1-3 is shown with the top of the housing removed. The motor 206 is a brushless direct current pancake motor sized to fit within a periphery of the belt 214 and positioned between the idler pulley 212 and the driving pulley 210. This arrangement minimizes the overall size of the pumping assembly (i.e., the motor 206, the gear set 208, the driving pulley 210, the idler pulley 212, and the belt 214) and, thus, permits a compact, highly portable and concealable design. The gear set 208 adds depth to the pumping assembly at the driving pulley 212 and motor 206 such that a space is formed on the same side of the pumping assembly as the idler pulley 212, and the battery 202 is positioned, at least partly, in the space. The user interface 104 is mounted on the front of the pump in this embodiment, and the controller 204 is immediately behind the user interface 204. The gear set 208 and battery 202 are near the controller 204, and the belt 214 is near the back of the pump. Positioning the belt 214 and rollers 216 at the rear of the medical pump, as opposed to closer to the center of the pump, locates the tube 108 closer to the body of the patient.

Figure 5:
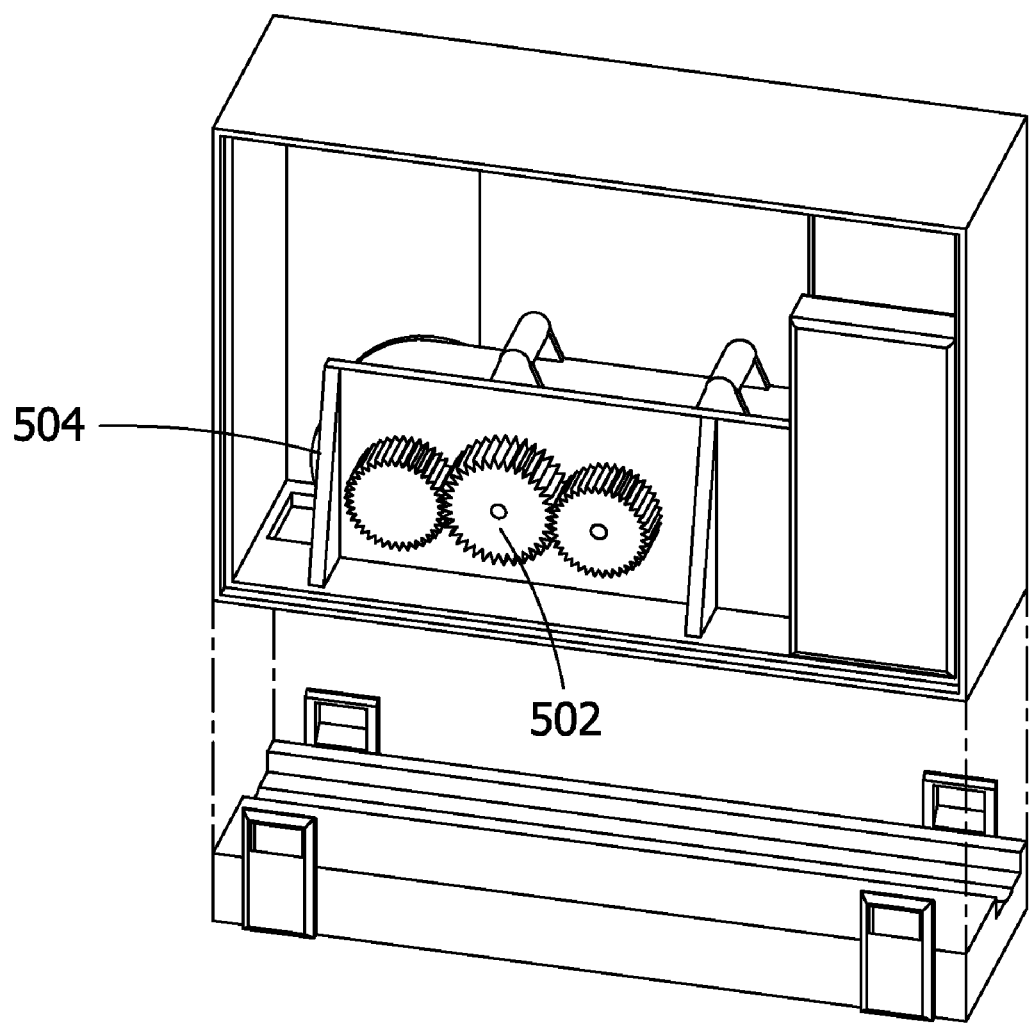
FIG. 5 is a perspective and exploded view of a compact medical pump having a back portion of a housing of the medical pump removed according to one embodiment of the invention.

According to another embodiment, FIG. 5 shows a perspective and exploded view from the back of a compact medical pump with the back of a housing of the pump removed. The medical pump of FIG. 5 functions in generally the same manner as the medical pump of FIGS. 1-4. The differences include the position and construction of some elements of the pump including the construction of the gear set, the orientation of the pumping assembly, and the location of the battery. For example, a gear set 502 of the medical pump has a 3-gear configuration as opposed to the 5-gear configuration in the embodiment of FIGS. 1-4. The gear set 502 has one gear attached to a motor of the medical pump, one gear attached to a driving pulley 504, and one idler gear between the gear on the motor and the gear on the driving pulley, all of which are on the same side of a frame member 618. It is to be understood that one skilled in the art will recognize various physical configurations that achieve suitable compactness within the scope of the present invention.

Figure 6:
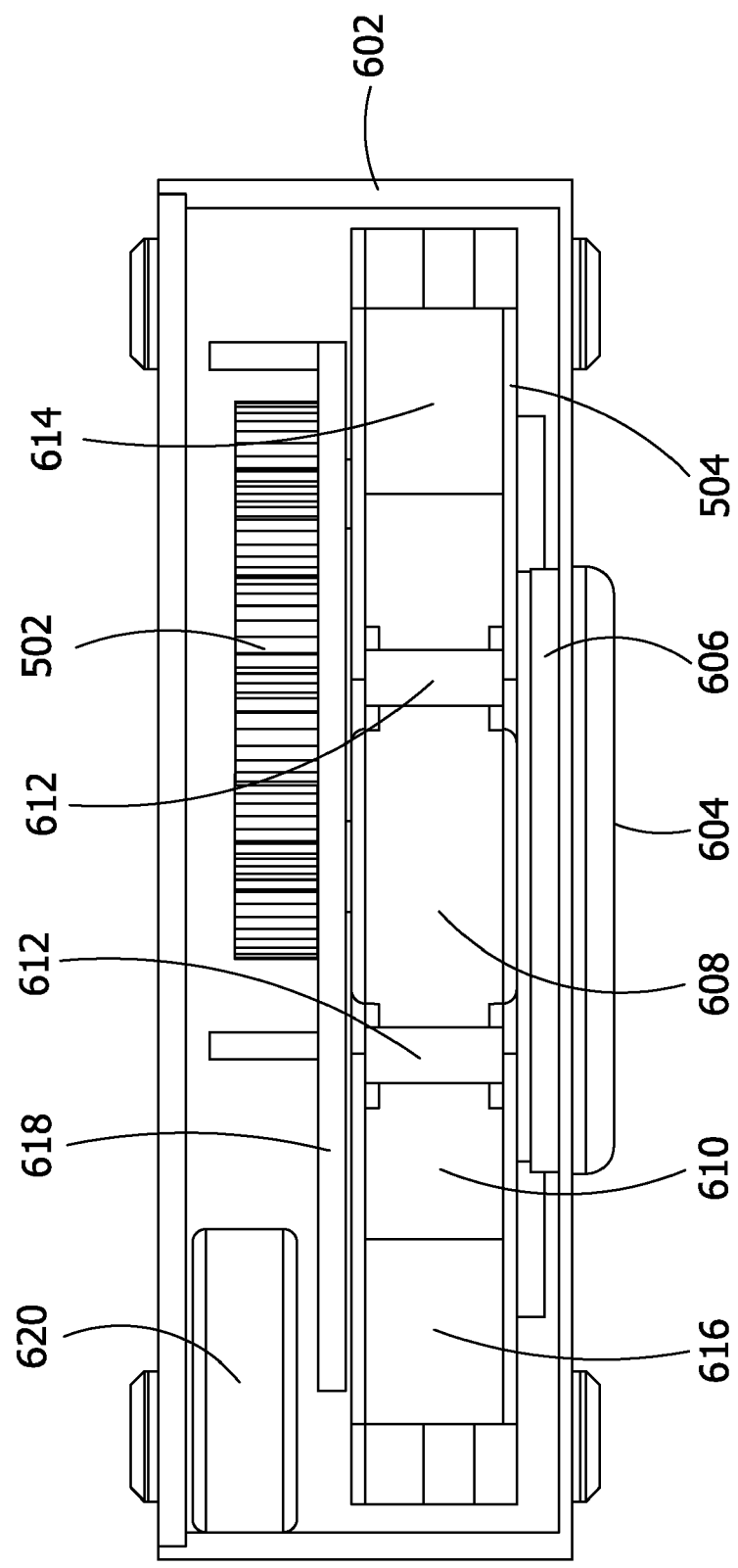
FIG. 6 is a top view of the compact medical pump of FIG. 5 having a top portion of a housing of the medical pump removed.

Referring to FIG. 6, a top view of the compact medical pump of FIG. 5 is shown with the top of the housing 602 removed. The housing 602 has a user interface 604 on a front side of the housing 602 with a controller 606 located immediately behind the user interface 604 inside the housing 602. In one embodiment, the controller 602 comprises a printed circuit board and integrated circuits. A pumping assembly of the medical pump is positioned behind the controller 606. The pumping assembly includes a motor 608, a gear set 502, a belt 610 having rollers 612, a drive pulley 614 and an idler pulley 616. A drive system of the pumping assembly comprises the motor 608, gear set 502, and pulleys 614, 616. The drive system is at least partially positioned within an interior space defined by an inner surface of the belt 610. The pumping assembly is supported by the frame member 618 extending vertically from the bottom of the housing 602. The frame member 618 may be integral with the housing 602, or may be fastened to the housing 602. The pumping assembly is oriented such that the belt 610 is located near the controller 606. The belt 610 is supported by the driving pulley 614 and the idler pulley 616, and the motor 608 is inside a periphery of the belt 616, between the two pulleys. The motor 608 is supported by the controller 606 such that no wires are needed to connect the motor 608 to the controller 606. The gear set 502 is behind the frame member 618 at the motor 608 and the driving gear 614 and a battery 620 is positioned adjacent to the gear set 502, behind the frame member 618. The embodiment illustrated in FIGS. 5-6 allows the motor 608 to be mounted to the controller 606 which eliminates parts (i.e., wires) and simplifies construction (i.e., eliminates mounting the motor 608 to the housing 602) of the pump.

Figure 7:
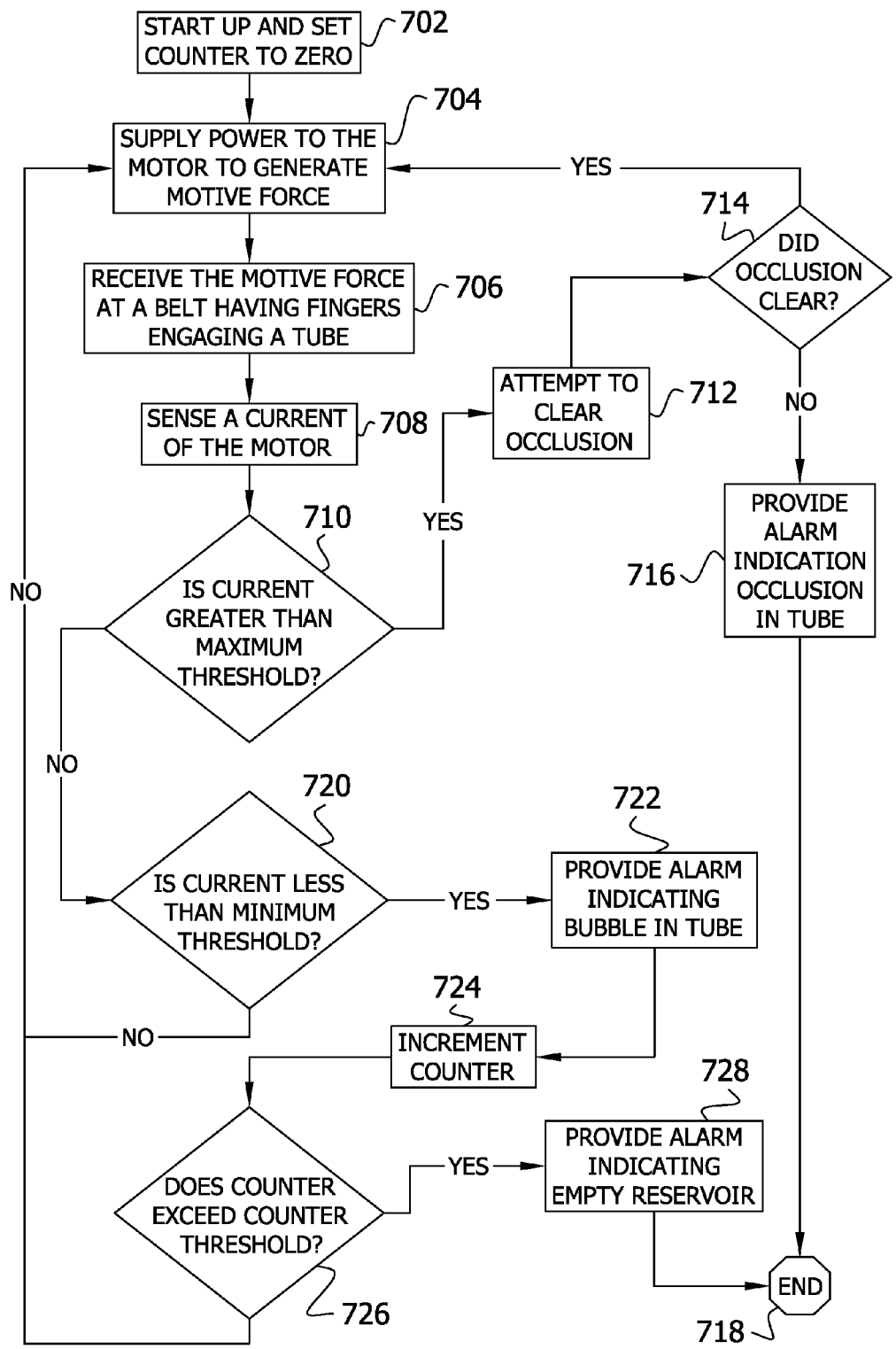
FIG. 7 is an exemplary flow diagram illustrating aspects of controller operations according to an embodiment of the invention.

The controller 204 includes switches for selectively providing power from the battery 202 to the motor 206 as a function of the pumping parameters described above, a current sensing circuit for determining the current provided to the motor 206, a memory for storing computer executable instructions for operating the pump, a processor for executing the stored instructions, and an input output circuit for interfacing with the user interface 104. Referring to FIG. 7, the controller 204 executes computer executable instructions for operating the pump. At 702, the controller initializes and sets a counter to zero. At 704, the controller causes power to be supplied to the motor to generate motive force. At 706, the motive force is received at a belt having fingers 215 engaging the tube 108 such that the fingers 215 move proximate the tube 108 in a peristaltic manner. At 708, the controller determines the current provided to the motor, and at 710, the controller determines whether the provided motor current exceeds a maximum current threshold. If the motor current exceeds the maximum current threshold, then the controller determines that the tube is occluded and attempts to clear the occlusion at 712. In one embodiment, the controller attempts to clear the occlusion by reversing the drive system a predetermined distance. At 714, the controller determines whether the attempt to clear the occlusion was successful by attempting to advance the drive system and monitoring the motor current. If the occlusion cleared, then the controller returns to 704 and supplies power to the motor to generate motive force and advance the belt and fingers relative to the tube. If the occlusion did not clear, then at 716, the controller provides an audio alarm or other indication via the user interface of the pump, and the controller ceases pumping operations at 718 until reset by the user (i.e., the power is cycled, or a reset button is pushed).

If the motor current did not exceed the maximum current threshold at 710, then at 720, the controller determines whether the motor current is less than a minimum threshold. If the current is not less than the minimum current threshold at 720, then the controller continues to supply power as a function of the pumping parameters to the motor at 704. If the current is less than the minimum current threshold at 720, then at 722, the controller determines that there is air (i.e., a bubble) in the tube in and provides an audio alarm or other error indication via the user interface of the pump. Optionally, the controller can determine whether the bubble exceeds a predetermined size and provide the alarm and end pumping operations only if the bubble exceeds the predetermined size. The controller determines whether the size of the bubble exceeds the predetermined size by monitoring the length of time that the motor current is below the current minimum and by monitoring how much the motor current undershoots the current minimum. At 724, the controller increments the counter, and at 726, the controller determines whether the counter exceeds the counter threshold. If the counter exceeds the counter threshold, then at 728, the controller determines that the reservoir is empty and provides an audio alarm or other indication of the empty reservoir to the user via the user interface of the pump. At 718, the controller causes pumping operations to cease. If the counter does not exceed the counter threshold at 726, then the controller continues to enable power to be supplied as a function of the pumping parameters to the motor at 704.

In an alternative embodiment, the controller 606 includes switches for selectively providing power from the battery 620 to the motor 608 as a function of the pumping parameters described above, a current sensing circuit for determining the current provided to the motor 608, a memory for storing computer executable instructions for operating the pump, a processor for executing the instructions, and an input output circuit for interfacing with the user interface 604. In this embodiment, controller 606 executes computer executable instructions for operating the pump in accordance with, for example, the operations shown in FIG. 7.

Although FIGS. 1-6 illustrate embodiments in which the belt has five fingers, it is contemplated that the belt may have any number of fingers without deviating from the scope of the invention.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may include aspects implemented with computer-executable instructions. The computer-executable instructions may be organized into one or more computer-executable components or modules. Aspects may be implemented with any number and organization of such components or modules. For example, aspects are not limited to the specific computer-executable instructions or the specific components or modules illustrated in the figures and described herein. Other embodiments of the invention may include different computer-executable instructions or components having more or less functionality than illustrated and described herein.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A medical pumping apparatus for administering a fluid to a patient via a pump set loaded therein, said pump set comprising a tube in fluid communication with a fluid source, said pumping apparatus comprising:
    a guide channel adapted for receiving a portion of the tube when the pump set is loaded in the pumping apparatus;
    a belt responsive to a motive force provided thereto for traveling proximate the portion of the tube received in the guide channel, said belt having at least one finger on an outer surface thereof, said finger engaging the portion of the tube received by the guide channel as the belt travels such that the tube is squeezed between the finger and an opposing surface of the guide channel to force the fluid through the tube from the fluid source toward the patient; and
    a drive system for providing the motive force to the belt, said drive system including a motor for generating the motive force, said motor being positioned substantially within an interior space defined by an inner surface of the belt.

2. The medical pumping apparatus of claim 1 wherein the finger comprises a roller for engaging the tube.

3. The medical pumping apparatus of claim 1 wherein the opposing surface of the guide channel comprises a platen against which the tube is squeezed by the finger.

4. The medical pumping apparatus of claim 1 further comprising a plurality of fingers evenly spaced about the outer surface of the belt for periodically engaging the portion of the tube received by the guide channel as the belt travels.

5. The medical pumping apparatus of claim 1 wherein the motor comprises a brushless direct current pancake motor.

6. The medical pumping apparatus of claim 1 wherein the drive system comprises:
    a plurality of pulleys for supporting the belt, at least one of said pulleys comprising a drive pulley engaging the inner surface of the belt; and
    a gear set engaging the motor and the drive pulley for transferring the motive force generated by the motor to the drive pulley for driving the belt.

7. The medical pumping apparatus of claim 1 further comprising:
    a user interface for displaying and receiving information relating to one or more pumping parameters; and
    a controller for selectively providing power to the drive system as a function of the pumping parameters.

8. The medical pumping apparatus of claim 7 further comprising a sensor for sensing a current of the motor; and wherein said controller is responsive to the sensed current for determining a fluid path characteristic of the pumping apparatus, said fluid path characteristic comprising at least one of:
    a bubble in the tube;
    an empty fluid source;
    a partial occlusion in the tube; and
    a complete occlusion in the tube.

9. The medical pumping apparatus of 7 further comprising a housing, said housing having a front for supporting the user interface, a bottom for supporting the guide channel, and a back, wherein the controller is positioned within the housing behind the user interface, the belt is positioned within the housing behind the controller, and a gear set of the drive system is positioned adjacent the back of the housing.

10. A medical pumping apparatus for administering a fluid to a patient via a pump set loaded therein, said pump set comprising a tube in fluid communication with a fluid source, said pumping apparatus comprising:
    a guide channel adapted for receiving a portion of the tube when the pump set is loaded in the pumping apparatus;
    a belt responsive to a motive force provided thereto for traveling proximate the portion of the tube received in the guide channel, said belt having a plurality of rollers evenly spaced about an outer surface of the belt, each of said rollers periodically engaging the portion of the tube received by the guide channel as the belt travels such that the tube is squeezed against an opposing surface of the guide channel to force the fluid through the tube from the fluid source toward the patient;
    a drive system positioned at least partially within an interior space defined by an inner surface of the belt for providing the motive force to the belt, said drive system including a motor for generating the motive force;
    a user interface for displaying and receiving information relating to one or more pumping parameters;
    a controller for selectively providing power to the drive system as a function of the pumping parameters, said controller being responsive to a current sensed in the motor for determining a fluid path characteristic of the pumping apparatus and said controller further selectively providing power to the drive system as a function of the determined fluid path characteristic; and
    a housing, said housing having a front for supporting the user interface, a bottom for supporting the guide channel, and a back, wherein the controller is positioned within the housing behind the user interface, the belt is positioned within the housing behind the controller, and a gear set of the drive system is positioned adjacent the back of the housing.

* * * * *